United States Patent [19]
Lee

[11] Patent Number: 6,004,609
[45] Date of Patent: Dec. 21, 1999

[54] GINSENG PROCESSING METHOD AND PROCESSED GINSENG PREPARED BY THE SAME

[76] Inventor: Sang-jun Lee, 221-28 Suyu 3-dong, Kangbuk-gu, Seoul, Rep. of Korea

[21] Appl. No.: 09/091,583

[22] PCT Filed: Jan. 17, 1997

[86] PCT No.: PCT/KR97/00009

§ 371 Date: Jun. 23, 1998

§ 102(e) Date: Jun. 23, 1998

[87] PCT Pub. No.: WO97/25884

PCT Pub. Date: Jul. 24, 1997

[30] Foreign Application Priority Data

Jan. 18, 1996 [KR] Rep. of Korea .......................... 96-1016
Jan. 16, 1997 [KR] Rep. of Korea .......................... 97-1181

[51] Int. Cl.$^6$ ....................................................... A23L 2/00
[52] U.S. Cl. ........................... 426/590; 426/597; 426/599; 426/638
[58] Field of Search .................................... 426/597, 599, 426/590, 638

[56] References Cited

U.S. PATENT DOCUMENTS 3,953,615   4/1976   Gupta et al. .

OTHER PUBLICATIONS

Database Abstract. FSTA. AN 90 (04):V0026. SU 1493232. Inventors: Avakyants et al, 1989.
Philadelphia Inquirer. Cool Down Tastefully with Brewed Iced Tea the Perfect Mix? The One You Do from Scratch. Author: A. Schloss. p. E01, Jun. 21, 1989.
Database Abstract (from Prompt). Product Alert article. Author: N/A. May 17, 1993.
Database Abstract. WPIDS. AN 95–253114 [33]. RU 2025992. Investors: Rokhlenko et al, Jan. 1995.
Database Abstract. WPIDS. AN 96–237546 [24]. RU 2045193. Inventors: Dzneladze et al, Oct. 1995.

*Primary Examiner*—Anthony J. Weier
*Attorney, Agent, or Firm*—Leydig, Voit & Mayer, Ltd.

[57] ABSTRACT

A ginseng processing method and a processed ginseng prepared by the processing method are provided. The ginseng processing method includes the steps of: mixing 10~99.5 wt % of grapes and/or wild grapes with 0.5~90 wt % of ginseng; adding water to the mixture of grapes and/or wild grapes with ginseng with a weight ratio of 1~10:1; heating the mixture at 45~130° C. for 1~70 hours; and cooling the heated mixture to room temperature. According to the ginseng processing method using grapes and/or wild grapes, the side effects caused by taking only ginseng are decreased or eliminated. Also, the browning of the ginseng is facilitated, reducing the amount of effort and time required for processing the ginseng. Also, the processed ginseng is acceptable to many persons in taste, aroma and color, and can be used in various forms for various purposes.

13 Claims, 1 Drawing Sheet

GINSENG PROCESSING METHOD AND PROCESSED GINSENG PREPARED BY THE SAME

This application has been filed under 35 USC 371 as a national stage application of PCT/KR97/00009 filed Jan. 1, 1997.

TECHNICAL FIELD

The present invention relates to a method for processing ginseng and processed ginseng obtained by the method, and more particularly, to a method for processing ginseng which inhibits unfavorable side effects of ginseng and a processed ginseng obtained through the method.

BACKGROUND OF THE INVENTION

Generally, ginseng is classified into green ginseng, white ginseng and red ginseng. Green ginseng is fresh ginseng which has not been dried after being dug from the ground, and white ginseng is obtained by removing fine root hair from the green ginseng, paring the ginseng, and then drying the pared ginseng in the sun. Red ginseng, the most significant among ginsen-related products, is obtained through a steaming process. Here, the color of the red ginseng is formed by a non-enzymatic browning reaction in the steaming process, particularly, an amino-carbonyl reaction and an automatic oxidation of polyphenol, and the above browning provide excellent characteristics to the ginseng.

According to a report by the World Health Organization (WHO), red ginseng, green ginseng and white ginseng commonly include 18 types of pharmaceutically effective components such as ginsenoside, Ro, $Ra_1$, $Ra_2$, $Ra_3$, $Rb_2$, $Rb_3$, Rc, Rd, Re, Rf, $Rg_1$, $Rg_2$, $Rg_3$, $Gh_1$, 20glc-Rf, $Q-R_1$ and $N-R_1$. Also, malonyl-$Rb_1$, malonyl-$Rb_2$, malonyl-Rc and malonyl-Rd are known to be included only in green ginseng and white ginseng, and $Rs_1$, $Rs_2$, $Rg_3(S)$, $Rh_2$, $N-R_4$, $Rg_2(R)$, $Rh_1(R)$ and $Rh_4$ are known to be included only in red ginseng. Thus, it is regarded that the medicinal effects of ted ginseng originates from 8 types of these components newly synthesized from the components included in green ginseng and white ginseng.

Ginseng, which has been used as a tonic in the Far East for a long time, is used in more than 500 prescription drugs among about 2000 basic prescriptions in traditional herbal medicine. Also, research into the medicinal effects of the ginseng as a mysterious plant has been conducted for about 100 years. Full-scale research into ginseng began when it was discovered that the medicinal effects of ginseng originates from saponin.

Saponin including a sapogenin as a non-sugar component continuously generates foam when agitated in a solution, and causes hemolysis. Also, saponin may stimulate a mucous membrane depending on circumstances and acts as a harmful factor to a blood vessel by forming a complex with blood cholesterol.

Generally, saponin of the ginseng has a useful medicinal effect rather than a toxic effect unlike the above-described general characteristics of saponin. However, the saponin of ginseng may cause a side effect depending on the human being. In the field of traditional herbal medicine, the physical constitution of a human being is classified into several types and a specific physical constitution to avoid taking ginseng is prescribed. Also, western medicine has reported the side effects of ginseng. As an example, a species of ginseng includes epedrin which causes a rise in blood pressure, metrorrhagia, ventricular arrythmia if taken for an extended period of time. According to a clinical study, it is reported that the above symptoms disappear when the intake of ginseng stops. Thus, the ginseng has been recognized as inappropriate for persons with high blood pressure.

Generally, bad feces, occurrence of fever, headaches or stimulation is known as side effects of ginseng. However, it has also been reported that the side effects of ginseng are considerably decreased through a process, e.g., a thermal process, compared with the case when ginseng is taken raw. Here, it is believed that this is because a high density component is changed into a low density component by the thermal process and side effects of various components of ginseng are neutralized by the thermal process.

Thus, when ginseng is processed, e.g, ginseng is boiled in water before being taken, troubles with digestion and metabolism can be slightly overcome while maintaining the medicinal effect of ginseng. However, the above processing method cannot solve the side effects of ginseng completely, so that traditional herbal medicine has prohibited patients with a cardiac disorder, a kidney disorder or allergies from taking ginseng. Also, research into materials which enable suppression of the side effects of ginseng by being used together with ginseng has not been conducted.

Also, generally, the ginseng is used and commercialized without being generally-processed and has a strong aroma. Thus, the ginseng may not be acceptable depending upon the race of the user. The acceptability of ginseng tea by human beings from all parts of the world was investigated twice. That is, the acceptability of ginseng tea in taste and aroma was investigated with respect to the visitors of the Geneva Invention Conference (1986) and Tokyo Invention Conference (1988). As a result, the acceptability with respect to taste and aroma of the ginseng tea was very low to Western people while acceptance was considerably high by the Japanese. Also, the acceptability by the Chinese was higher than that by the Japanese. Thus, it is difficult to commercialize the ginseng as a worldwide health food or a delicacy, without making the taste to be acceptable to persons of all race.

The Applicant has practiced traditional herbal medicine for about 30 years and has studied ginseng processing methods for about 10 years with confidence that the ginseng has favorable effects regardless of the physical characteristics of the human being. Also, the inventor has conducted research on a material which can be added in the processing of ginseng in order to suppress the side effects of the ginseng and offset the strong aroma. First, various edible plants were selectively added during the processing of the ginseng in order to find a material which can offset the strong aroma of the ginseng. Then, the ginseng processed together with the selected plant was taken by the human being exhibiting side effects of the ginseng, resulting in a remarkable effect.

DISCLOSURE OF THE INVENTION

It is an object of the present invention to provide a method for processing ginseng by which the side effects of ginseng, caused by the independent use of ginseng, is suppressed and browning of the ginseng is facilitated.

It is another object of the present invention to provide processed ginseng obtained by the above method for processing the ginseng.

To achieve the first object of the present invention, there is provided a method for processing ginseng comprising the steps of: mixing 10~99.5 wt % of grapes and/or wild grapes (e.g., non-wild, domestic) with 0.5~90 wt % of ginseng; adding water to the mixture of grapes and/or wild grapes with ginseng with a weight ratio of 1~10:1; heating the mixture at 45~130° C. for 1~70 hours; and cooling the heated mixture to room temperature.

Preferably, the method for processing ginseng further comprises the step of filtering the cooled mixture to process the produced filtrate into a beverage, after the step of cooling the heated mixture.

Preferably, the method for processing ginseng further comprises the step of filtering the cooled mixture and drying the produced filtrate, after the step of cooling the heated mixture. Here, the drying method does not have any restriction.

More preferably, the method for processing ginseng further comprises the step of processing the dried mixture into a form selected from the group consisting of a powder, tablets, pills, granules, hard capsules and soft capsules, after the step of drying the filtrate.

Preferably, the ginseng is one selected from the group consisting of green ginseng, white ginseng and red ginseng.

To achieve the second object of the present invention, there is provided a processed ginseng prepared by the ginseng processing method described above.

Preferably, the processed ginseng is in the form of one of a liquid, a powder, granules, a gel, a sol, capsules and pills.

The processed ginseng may be used to make a ginseng tea, or a ginseng beverage, or a tonic for recovering from fatigue.

As a material added in the processing of ginseng, grapes can be used. Grapes can include reducing sugars (such as glucose and fructose), pectin, malic acid, tartaric acid, tannin, nitrogen containing compounds, citric acid, ash, amino acid, iron, magnesium, inositol, carbohydrate, protein, leucoanthocyanidine and pycnogenol. Here, tannin, malic acid and citric acid help digestive function, and pycnogenol and leucoanthocyanidine function as an anti-aging and detoxicating material. When grapes having the above properties are mixed with ginseng, the side effects of the ginseng such as difficulty in digestion and occurrence of fever, which is caused by the independent use of the ginseng, can be suppressed. Also, sugar, amino acid and nitrogen containing compound facilitate the browning of ginseng which helps the digestion of ginseng. Also, wild grapes which belong to the grape family have a similar function to grapes.

Preferably, a mixing ratio of grapes and/or wild grapes and the ginseng is controlled according to the individual taste and the use of a processed ginseng. Also, further modifications and alterations will occur to those skill in the art within the spirit and scope of this invention

DETAILED DESCRIPTION

Figure 1:
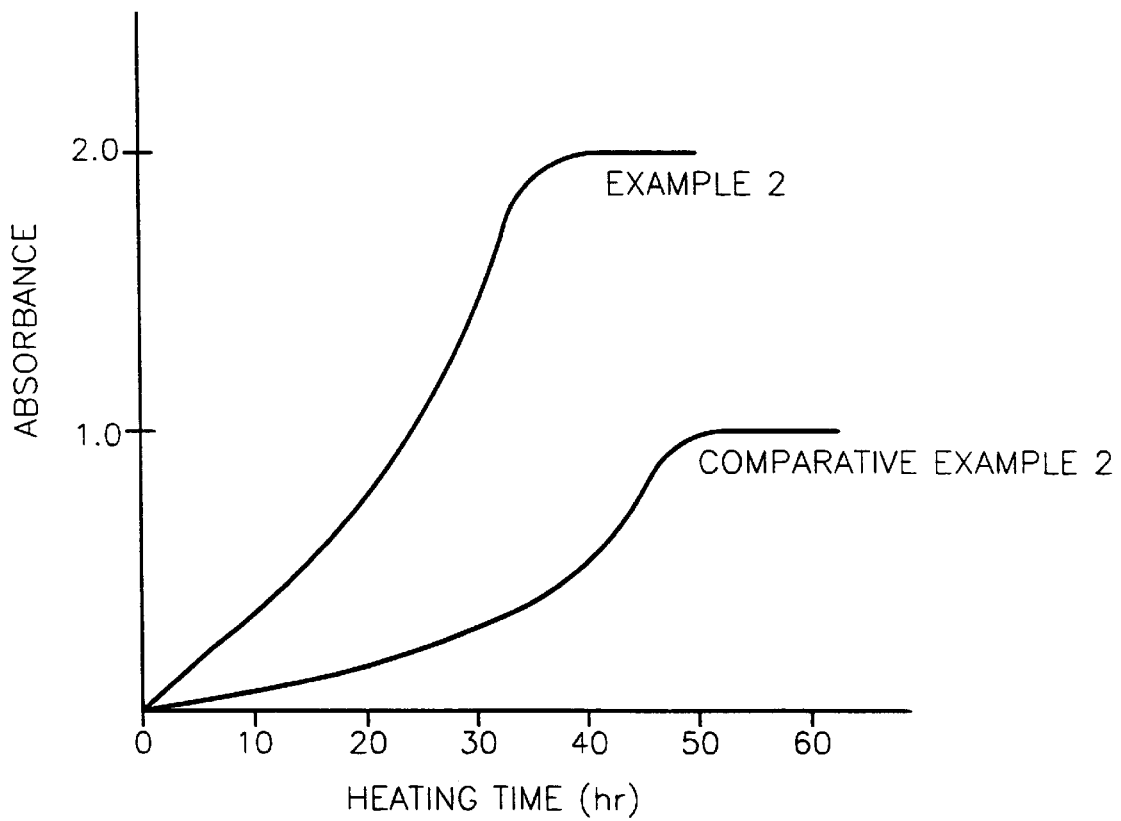
FIG. 1 is a graph showing the change in the degree of browning according to the heating time when processing ginseng by a heating method.

First, 10~99.5 wt % of grapes and/or wild grapes and 0.5~90 wt % of ginseng are put in a container, and water is poured thereinto and then heated. Here, it is preferable to continuously heat the mixture until the degree of browning reaches the maximum level, particularly, at 45~130° C. for 1~70 hours. That is, the ginseng can be processed at a ripening temperature of 60° C. or less, or at a low temperature of 60~80° C., or at a high temperature of 80~100° C. When the green ginseng in water is heated at 95° C., the maximum degree of the browning can be achieved after 50~60 hours. However, when the ginseng is heated together with grapes and/or wild grapes according to the present invention, the maximum degree of browning can be achieved within 35 hours. That is, the time required for achieving the maximum degree of browning is remarkably reduced. When browning is achieved to an appropriate level, the heating process is terminated and then the resultant mixture is cooled. If required, the mixture is dried and then processed into a powder according to a conventional method.

The processed ginseng of the present invention may be formulated in various forms such as a liquid, a powder, granules, a tablet, a gel, a sol, a capsule or a pill. The processed ginseng can be used in many applications. That is, the processed ginseng may be used in ginseng tea or other ginseng beverage ,which can be made according to a conventional processing methods.

The degree of browning occurring in the processing of the ginseng was determined by measuring the absorbance of a mixture solution with respect to time at a predetermined wavelength (440 nm) using a spectrophotometer with respect to time. Here, the absorbance of distilled water at the same wavelength is used as a reference.

Hereinafter, examples of the present invention will be described in detail, however, the present invention is not limited to the examples.

EXAMPLE 1

300 ml of water was poured into a container including 10 g of white ginseng and 90 g of grapes and then the resultant mixture was heated at about 75° C. for 40hours. Then, the heated mixture was cooled and then filtering, resulting in a liquid processed ginseng ("processed ginseng tea").

EXAMPLE 2

400 ml of water was poured into a container including 40 g of green ginseng and 60 g of grapes and then the resultant mixture was heated at about 95° C. until the degree of browning did not change, resulting in a processed ginseng. Here, the degree of browning was measured at predetermined intervals, and the result is shown in FIG. 1.

EXAMPLE 3

400 ml of water was poured into a container including 50 g of green ginseng and 50 g of grapes and then the resultant mixture was heated at about 90° C. for about 8 hours. Then, the mixture was cooled to 60° C. and maintained at the temperature for 5 hours to form a concentrate and then dried to form a granule form according to a general method.

EXAMPLE 4

500 ml of water was poured into a container including 75 g of green ginseng and 25 g of grapes and then the resultant mixture was heated at about 100° C. for about 3 hours. Then, the mixture was cooled and then filterted. Then, the filtrated solution was processed into a powder by a general method, resulting in a powdered processed ginseng.

EXAMPLE 5

500 ml of water was poured into a container including 20 g of red ginseng and 80 g of grapes and then the resultant mixture was heated at about 70° C. for about 50 hours. Then, the mixture was cooled and then filtering. Then, the filtrated solution was processed into a powder by a general method, resulting in a powdered processed ginseng.

EXAMPLE 6–10

Processed ginsengs were obtained by the same processes as those of Examples 1–5, except wide grapes were used instead of grapes.

EXAMPLE 11

A processed ginseng was obtained by the same process as that of Example 3, except 25 g of grapes and 25 g of wild grapes were used instead of 50 g of grapes.

Comparative Example 1

A liquid processed ginseng ("natural ginseng tea") was obtained by the same process as that of Example 1, except grapes were not added.

Comparative Example 2

A processed ginseng was obtained by the same process as that of Example 2, except grapes were not added. Then, the degree of browning was measured at predetermined intervals, of which the result is shown in FIG. 1.

Comparative Example 3

A granule type processed ginseng was obtained by the same process as that of Example 3, except grapes were not added.

Evaluation Test 1

The degree of browning was measured with respect to the processed ginsengs obtained in Example 2 and the Comparative Example 2, of which the results are shown in FIG. 1. As shown in FIG. 1, in the processed ginseng of Example 2, the degree of browning is higher and the time required for reaching the maximum degree of browning is shorter than the processed ginseng of Comparative Example 2. That is, when grapes are mixed with ginseng, the browning of the ginseng is facilitated, so that favorable properties can be obtained within a short time period compared with the case where ginseng is used. Here, the browning was caused by the change of components included in ginseng, rather than by the change in color of grapes.

This was verified by a high performance liquid chromatography (HPLC).

That is, each of three samples including grape powder (control sample 1), ginseng powder (control sample 2) and the powdered processed ginseng (experimental sample) obtained from Example 4 was dissolved in water and then ether was added thereto. Each mixture was vigorously mixed and then left for a predetermined time. After removing an ether layer, the remaining water layer was extracted using butanol. The fraction extracted using butanol was dried under a vacuum. Then, the remaining product was dissolved in methanol to prepare a sample for the HPLC with respect to the above three samples. As a result, a chromatogram of the experimental sample exhibited new peaks which did not appear in the chromatograms of the control samples 1 and 2. The newly separated constituents corresponding the new peaks are regarded as a material for suppressing the side effects of ginseng.

Evaluation Test 2

The liquid processed ginsengs prepared in Example 1 and Comparative Example 1 were diluted to an appropriate concentration to produce ginseng beverages. Then, an overall preference test and a color preference test were performed with respect to the prepared ginseng beverages using an arbitrarily selected group. Here, the selected group included eight males and eight female, aged 16 through 65. As a result, 14 among the 16 preferred the Example 1 in the overall preference test, and 15 among the 16 preferred the Example 1 in the color preference test.

Evaluation Test 3

This test determines whether the processed ginseng does not cause the above-mentioned side effects of ginseng any more for a group having unfavorable symptoms such as trouble with digestion, occurrence of fever and edema against ginseng. The granular processed ginseng prepared in Example 3 was taken by each of 30 males and females, aged 16 through 65, having severe unfavorable symptoms against ginseng, for 10 days (1~3 g dose, 1~3 times per day). As a result, 12 persons showed slight unfavorable symptoms. However, the remaining did not show any unfavorable symptoms at all, and the feces taken from the persons were normal, and a fever or a rise in blood pressure did not occur. The operational mechanism is yet unknown, however, it is regarded that constituents and enzymes of the grape facilitate the browning of the ginseng, suppress the side effects of ginseng, and raises the medicinal effect of ginseng.

Evaluation Test 3 was repeatedly performed with respect to the processed ginsengs prepared in other examples by selecting smaller group than the above. As a result, the side effects of the ginseng was greatly suppressed with a slight difference in the degree of the effect.

Evaluation Test 4

An animal experiment was performed using mice in order to find whether the processed ginseng of the present invention shows the side effect of the ginseng such as edema.

That is, 18 forty-day-old mice were randomly divided into three groups: an experimental group, a control group 1 and a control group 2, each with 6 mice. The processed ginseng prepared in Example 4 was dissolved in a saline and injected into the abdominal cavity for the experimental group once per day for 11 days, each dose consisting of 25 mg (dry weight)/1kg body weight. Also, the ginseng powder was administrated to the control group 1 in the same manner as that used for the experimental group. After two hours from each administration, the thickness of the paw, that is, the thickness between the instep and sole of the paw, was measured with respect to the experimental group and the control group using a microcaliper. Meanwhile, only saline was administrated to the control group 2in the same manner as above, and then the thickness of paw was measured in the same manner a reference indicating paw thickness increase due to growth. Then, the reference values were subtracted from the values of the paw thicknesses measured in the experimental group and the control group 1. As a result, edema was remarkably decreased in the experimental group as the days passed while the decrease of the edema was not shown in the control group 1. That is, the degree of edema was 0.018±0.029 mm at the seventh day and 0.007±0.004 mm at the eleventh day, respectively, in the experimental group. Meanwhile, it was 0.027±0.044 mm at the seventh day and 0.025±0.014 mm at the eleventh day, respectively, in the control group 1.

Evaluation Test 5

An animal experiment was performed using mice in order to find whether the processed ginseng of the present invention shows a tonic effect of the natural ginseng.

That is, 30 forty-day-old mice were randomly divided into three groups, an experimental group, a control group 1 and a control group 2, each with 6 mice. The processed ginseng prepared in Example 4 was dissolved in a saline and injected into the abdominal cavity for the experimental group once per day for a week, each dose consisting of 20 mg (dry weight)/1 kg body weight. Also, the ginseng powder was administrated to the control group 1 in the same manner as that used for the experimental group while the control group 2 did not take anything. After one hour from the final administration, a swimming test was performed with respect to each group in a water bath at room temperature. For continuous swimming, a ring weighing ⅓ the weight of the average weight of the mice was tied to the tail of the mouse. Then, the length of time the mouse swam until it died was measured. As a result, the average times of the control group 2 and the control group 1 were 45 and 55 minutes, respectively. Meanwhile, the average time of the experimental group was 64 minutes.

Industrial Applicability

As described above, according to the ginseng processing method of the present invention using grapes and/or wild grapes, the side effects such as trouble with digestion and fever, which were caused by taking only ginseng, are decreased or eliminated. Also, the browning of the ginseng is facilitated, reducing the amount of effort and time required for processing the ginseng. Also, the processed ginseng is acceptable to many persons in taste, aroma and color. Also, the processed ginseng prepared in a richly concentrated solution can easily be taken by everyone for maintaining health and recovering from fatigue. In addition, the processed ginseng in a powder or liquid form can be used as a tea or a beverage. The processed ginseng may be prepared in tablets, pills, granules, hard capsules and soft capsules to be used readily at any time and any place.

What is claimed is:

1. The method for processing ginseng comprising the steps of:

mixing from about 10% to about 99.5% by wt grapes with from about 0.5% to about 90% by wt ginseng;

adding water to the mixture of said grapes with ginseng with a weight ratio of from about 1:1 to about 10:1;

heating the mixture at a temperature of from about 45° C. to about 130° C. for a period of from about 1 hour to about 70 hours; and cooling the heated mixture to room temperature.

2. The method for processing ginseng as claimed in claim 1, further comprising the step of:

filtering the cooled mixture to process the filtrate into a beverage, after said step of cooling the heated mixture.

3. The method for processing ginseng as claimed in claim 1, further comprising the step of:

filtering the cooled mixture and drying the filtrate, after said step of cooling the heated mixture.

4. The method for processing ginseng as claimed in claim 3, further comprising the step of:

processing the dried mixture into a form selected from the group consisting of a powder, tablets, pills, granules, hard capsules and soft capsules, after said step of drying the filtrate.

5. The method for processing ginseng as claimed in claim 1, wherein the ginseng is one selected from the group consisting of green ginseng, white ginseng and red ginseng.

6. A processed ginseng prepared by the ginseng processing method of claim 1.

7. The processed ginseng as claimed in claim 6, wherein said processed ginseng is in the form of one of a liquid, a powder, granules, a gel, a sol, capsules and pills.

8. The processed ginseng as claimed in claim 6, wherein said processed ginseng is a beverage.

9. The method for processing ginseng as claimed in claim 1, wherein said grapes comprise wild grapes.

10. The method for processing ginseng as claimed in claim 1, wherein said grapes comprise wild and non-wild grapes.

11. The processed ginseng of claim 8, wherein said beverage is a tea.

12. The method of claim 1, whereby the concentration of at least one ginsenoside is increased.

13. A processed ginseng as claimed in claim 6, which is substantially free of side effects to humans.

* * * * *